United States Patent
Paul

(10) Patent No.: US 10,451,268 B2
(45) Date of Patent: Oct. 22, 2019

(54) METHOD FOR EVALUATING THE CLOGGING OF A HEAT EXCHANGER

(71) Applicant: ELECTRICITE DE FRANCE, Paris (FR)

(72) Inventor: Nicolas Paul, Montreuil (FR)

(73) Assignee: ELECTRICITE DE FRANCE, Paris (FR)

( * ) Notice: Subject to any disclaimer, the term of this patent is extended or adjusted under 35 U.S.C. 154(b) by 523 days.

(21) Appl. No.: 14/653,473

(22) PCT Filed: Dec. 19, 2013

(86) PCT No.: PCT/EP2013/077341
§ 371 (c)(1),
(2) Date: Jun. 18, 2015

(87) PCT Pub. No.: WO2014/096168
PCT Pub. Date: Jun. 26, 2014

(65) Prior Publication Data
US 2015/0346156 A1 Dec. 3, 2015

(30) Foreign Application Priority Data
Dec. 19, 2012 (FR) .................... 12 62330

(51) Int. Cl.
*G01N 27/90* (2006.01)
*F22B 37/00* (2006.01)
*G21C 17/017* (2006.01)

(52) U.S. Cl.
CPC ............ *F22B 37/003* (2013.01); *F22B 37/00* (2013.01); *G01N 27/9033* (2013.01); *G01N 27/9046* (2013.01); *G21C 17/017* (2013.01)

(58) Field of Classification Search
CPC .............. B24B 49/105; G01N 27/9046; G01N 27/9033; G21C 17/017; F22B 37/003
See application file for complete search history.

(56) References Cited

U.S. PATENT DOCUMENTS

2011/0022333 A1   1/2011   Griffith et al.

FOREIGN PATENT DOCUMENTS

FR        2993090           1/2014

OTHER PUBLICATIONS

Beddek, Progagtion of Uncertainties in Finite Element Models in Electromagnetism—Application to Non-Destructive Testing by Foucault Currents Chapter 4, Jun. 2012, pp. 3-35.*

(Continued)

*Primary Examiner* — Sujoy K Kundu
*Assistant Examiner* — L. Anderson
(74) *Attorney, Agent, or Firm* — Womble Bond Dickinson (US) LLP

(57) ABSTRACT

A method for evaluating the clogging of the passages of a tube support plate of a tube heat exchanger, in which an eddy current probe is passed through a tube of the exchanger and a measurement signal is measured with the probe to evaluate the clogging at the downstream edge of a tube support plate. A lower (upper, respectively) edge signal corresponding to the probe passing the downstream (upstream, respectively) edge of the tube support plate is determined from the measurement signal. The impulse response of the probe is estimated. The lower edge signal is deconvolved (530) by the impulse response estimation. The clogging is evaluated (533) by analyzing (532) the lower edge signal thus deconvolved.

11 Claims, 11 Drawing Sheets

(56) References Cited

OTHER PUBLICATIONS

NDT Resource Center, Multiple Frequency Techniques, Jul. 10, 2002, pp. 1-2.*
French Search Report, dated Sep. 6, 2013, French Application No. FR1262330.
International Search Report with English Language Translation, dated Feb. 10, 2014, Application No. PCT/EP2013/077341.
Basart, John P., et al., "Distinguishing signals from noise in eddy current inspection of steam generator tubes", *SPIE proceedings*, vol. 2944, (Nov. 15, 1996), 201-209.
Beddek, Karim, "Propagation d'incertitudes dans les modèles éléments finis en électromagnétisme", *Application au contrôle non destructif par courants de Foucault*, Retrieved from the Internet: http://l2ep.univ-lillel.fr/fileupload/file/theses/TheseKarimBeddek.pdf, (Jun. 29, 2012), 93-97.
Bentoumi, et al., "On-line rail defect diagnosis with differential eddy current probes and specific detection processing", *The European Physical Journal—Applied Physics*, vol. 23, No. 3, (Sep. 30, 2003), 227-233.
Chatellier, et al., "Tube support plate blockage evaluation with televisual examination and eddy current analysis", *AIP conference proceedings*, vol. 1096, (Jul. 25, 2008), 766-773.
Yang, Guang, et al., "Nonlinear, non-stationary image processing technique for eddy current NDE", *AIP conference proceedings*, vol. 1430, (Jul. 22, 2011), 689-696.

* cited by examiner

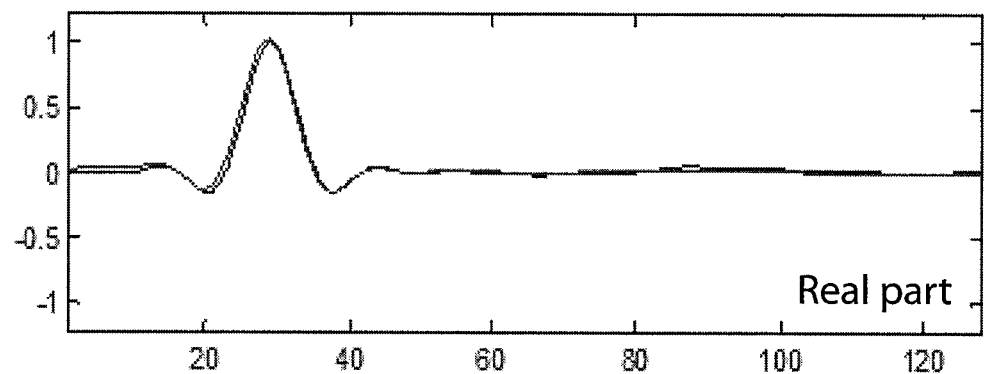
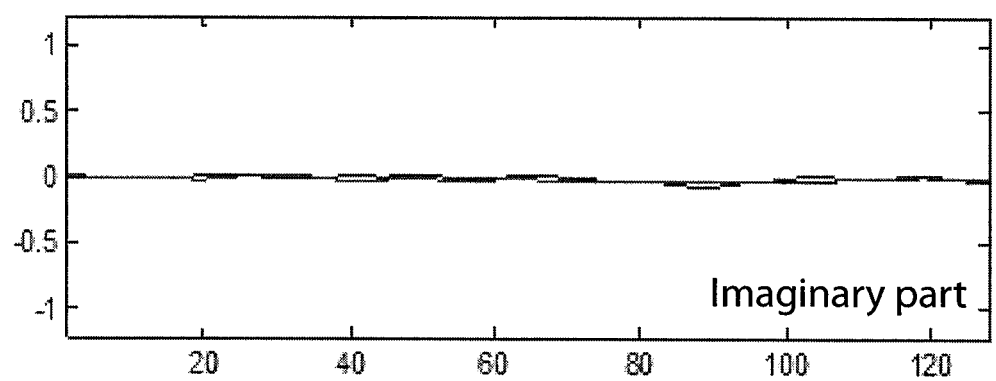
FIG 7

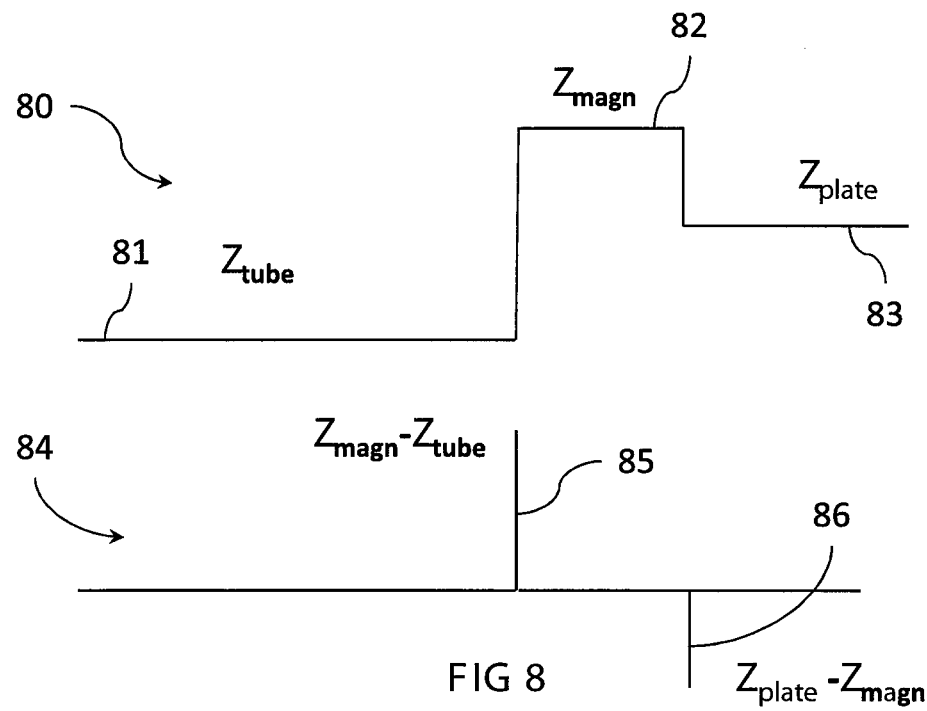
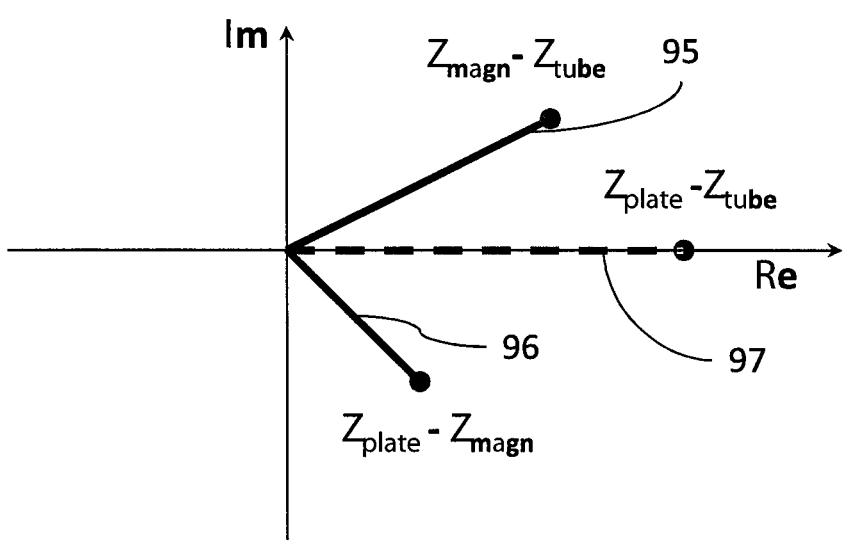
FIG 9

METHOD FOR EVALUATING THE CLOGGING OF A HEAT EXCHANGER

TECHNICAL FIELD AND CONTEXT OF THE INVENTION

The present invention relates, generally speaking, to the field of the inspection of the tubes of a tube heat exchanger. More precisely, the invention relates to a method for evaluating the clogging of the passages of a tube support plate of a tube heat exchanger, said passages being made along the tubes and serving for the circulation of a fluid in said heat exchanger through said plate.

A steam generator is generally composed of a bundle of tubes in which hot fluid circulates and around which circulates the fluid to be heated. For example, in the case of a steam generator of a PWR type nuclear power plant, the steam generators are heat exchangers that use the energy of the primary circuit from the nuclear reaction to transform the water of the secondary circuit into steam, which will supply the turbine and thus produce electricity.

The steam generator brings the secondary fluid from a liquid water state to the steam state just at the saturation limit, using the heat of the primary water. Said primary water circulates in tubes around which the secondary water circulates. The outlet of the steam generator is the highest point in temperature and pressure of the secondary circuit.

The exchange surface, physically separating the two circuits, is thus constituted of a tubular bundle, composed of 3500 to 5600 tubes, according to the model, in which circulates the primary water taken to high temperature (320° C.) and high pressure (155 bars).

These tubes of the steam generator are maintained by tube support plates generally arranged perpendicularly to the tubes that pass through them.

In order to allow the fluid which vaporises to pass, the passages of these tube support plates are foliated, that is to say that their shape has lobes around the tubes. Since the water goes from the liquid state to the vapour state, it deposits all the materials that it contains. If the depositions of material take place in the lobes, they reduce the free passage: this is clogging, which is thus the progressive closing up, by depositions, of the holes intended for the passage of the water/steam mixture.

FIG. 1 schematically illustrates a top view of a foliated passage in a tube support plate 10, through which passes a tube 11. The lobes 12a and 12b enable water to pass through the tube support plate 10 along the tube 11, thereby enabling the circulation of water in the steam generator. A deposition 13 is visible at the lobe 12b, clogging said lobe 12b. The deposition may be situated on the tube side and/or on the plate side.

The clogging leads to modifications of the flow of water in the steam generator, and thus favours the onset of excessive vibrations of the tubes, as well as inducing significant mechanical stresses on the internal structures of the steam generator. This degradation thus has effects both on the safety and on the performances of the installations. It is thus indispensable to have good knowledge of the nature and the evolution of this degradation.

At present, the only non-destructive examination system that is capable of accessing the totality of the tube/tube support plate intersections of steam generators is the axial eddy current probe (SAX probe). Eddy currents appear in a conductive material when the adjacent magnetic flux is varied. A multifrequency eddy current probe is passed through a tube of said exchanger and a measurement signal is measured with said probe according to the environment in which the probe is situated, from which it is possible to extract information regarding anomalies in the heat exchanger.

A variation of the magnetic induction, typically by a coil in which an alternating current circulates, generates eddy currents, of which the variation induced by the magnetic field is detected. Typically, the voltage difference generated by the variation of impedance of the coil is measured.

The exploitation of the measurement signals of this eddy current probe does not result in a lengthening of the shutdown of the steam generator, since said eddy current probe is already used during unit shutdowns, particularly for inspecting the integrity of the tubes of the steam generator.

Said eddy current probe, initially intended for the detection of damage to the tubes, is also sensitive to clogging. Furthermore, the interpretation of this signal is at present performed manually by specialised operators, which is very long, of the order of around a week of processing for the analysis of a single steam generator. Furthermore, the intervention of an operator to plot measurements from analysis software often gives rise to a bias that is difficult to quantify.

Moreover, the measurement signal is not calibrated and is noisy, such that its exploitation may prove to be difficult.

The evaluation of the clogged aspect of a foliated passage by an operator from the measurement signal is moreover very unreliable, being generally carried out empirically given the signal received and its comparison with other signals corresponding to other passages, the condition of which is known, for example by televisual inspection.

DESCRIPTION OF THE INVENTION

A general aim of the invention is to overcome all or part of the defects of the methods of the prior art for evaluating the clogging of foliated passages around tubes in tube support plates.

A method is in particular proposed for evaluating the clogging of the passages of a tube support plate of a tube heat exchanger, said passages being made along the tubes for a fluid to pass through the tube support plate, in which an eddy current probe is passed through a tube of said exchanger and a measurement signal is measured with said probe according to the environment in which the probe is situated, characterised in that in order to evaluate the clogging at the downstream edge of a tube support plate:

- a lower edge signal corresponding to the probe passing the downstream edge of the tube support plate is determined from the measurement signal;
- an upper edge signal corresponding to the probe passing the upstream edge of the tube support plate is determined from the measurement signal;
- the impulse response of the probe is estimated;
- the lower edge signal is deconvolved by means of said impulse response estimation;
- the clogging is evaluated by analysing the lower edge signal thus deconvolved.

This method is advantageously completed by the following characteristics, taken alone or in any of the technically possible combinations thereof:

- the probe acquires at least in part the measurement signal in differential mode;
- the measurement signal is a multifrequency signal composed of at least two signals at different frequencies, and the lower edge signal and the upper edge signal result from linear combinations of at least two signals at frequencies different to said measurement signal;

the linear combination involves a complex coefficient optimised to minimise the signal power along the tube outside of zones where plates are present;

the impulse response of the probe is estimated from the upper edge signal;

the deconvolution of the lower edge signal by means of the impulse response estimation of the probe is realised using a filter constructed from said impulse response estimation;

the frequency response of the filter is an approximation of the inverse of the Fourier transform of the impulse response of the probe;

the filter is a Wiener filter and the deconvolution is a Wiener deconvolution;

the frequency response of the Wiener filter is of the form:

$$G[f] = \frac{H^*[f]}{\|H[f]\|^2 + \frac{B[f]}{S[f]}}$$

with the exponent * designating the complex conjugation, $H[f]$ the Fourier transform of the impulse response of the probe, $S[f]$ the power spectral density of the signal to be estimated and $B[f]$ the power spectral density of the noise;

the impulse response of the probe $h[n]$ is estimated from the response of the probe $z_{upp}[n]$ to the passage of the upstream edge of the tube support plate by the probe according to:

$$h[n] = -z_{upp}[-n]$$

a filtering by a low pass filter is applied to the deconvolved lower edge signal, the cut-off frequency of said low pass filter being determined by means of a standard deviation of a Gaussian function constituting an approximation of the real part of an impulse of the signal corresponding to the probe passing a clean edge of a tube support plate;

the analysis of the deconvolved lower edge signal comprises the analysis of the real part and the imaginary part of said deconvolved lower edge signal;

the analysis of the deconvolved lower edge signal comprises the definition of indicators corresponding to pairs of extremes of physical quantities of the imaginary part of the lower edge signal.

The invention also relates to a computer programme product comprising programme code instructions for the execution of the steps of the method according to the invention, when said programme is run on a computer.

DESCRIPTION OF THE FIGURES

Other characteristics, aims and advantages of the invention will become clear from the description that follows, which is purely illustrative and non-limiting, and which must be read with regard to the appended drawings, among which:

FIGS. 6 and 7 illustrate the profile of the deconvolved signals in the clean plate configuration;

FIGS. 8 and 9 illustrate the changes of impedance recorded by an ideal probe in a configuration of passage clogged by a deposition of magnetite situated at the same level as the lower edge of the tube support plate;

DETAILED DESCRIPTION

Extraction of the Useful Parts of the Measurement Signal

In order to carry out the evaluation of the clogging of the foliated passages 12a, 12b of the tube support plates 10, the measurement signal preferably undergoes a pre-processing aiming in particular to extract therefrom the parts corresponding to the probe passing the tube support plates. The extraction of these useful parts of the measurement signal may be done in different ways. French patent application no 1256584 discloses a preferential embodiment for determining the position of the tube support plates, the principles of which are recalled hereafter.

A multifrequency eddy current probe is passed through a tube 11 of said exchanger and a measurement signal is measured with said probe according to the environment in which the probe is situated. The measurement signal is thus acquired by the axial eddy current probe during its movement in the tube 11 of the steam generator. This measurement signal is multifrequency, and is in complex form, with real and imaginary components. Within the scope of this description, a signal will be considered with complex components according to three frequencies from three acquisition channels, of which two in differential modes noted $z_1[n]$ and $z_3[n]$ and one in absolute mode noted $z_A[n]$. The frequencies are for example comprised in the range 100-600 kHz.

The probe carrying out a back and forth journey in the tube, preferably the signals corresponding to the movement phase are chosen where the probe is pulled by the mechanism which moves, typically during its return. In fact, this results in a better mechanical stability of the probe, and consequently a more regular velocity thereof.

The selection of the part of the signal of the probe corresponding to the return of the probe is based on the detection of an important drop of the voltage measured at the moment where the probe switches round to travel the tube in the return direction. The selection of a measurement signal limited to a single direction of the probe also makes it possible to limit the quantity of data to save and to process.

Given the sensitivity of the acquisitions of the eddy current signals to the acquisition conditions, at the switching over of the probe and in order to standardise the signals analysed, a prior step of calibration is preferably implemented.

Figure 1:
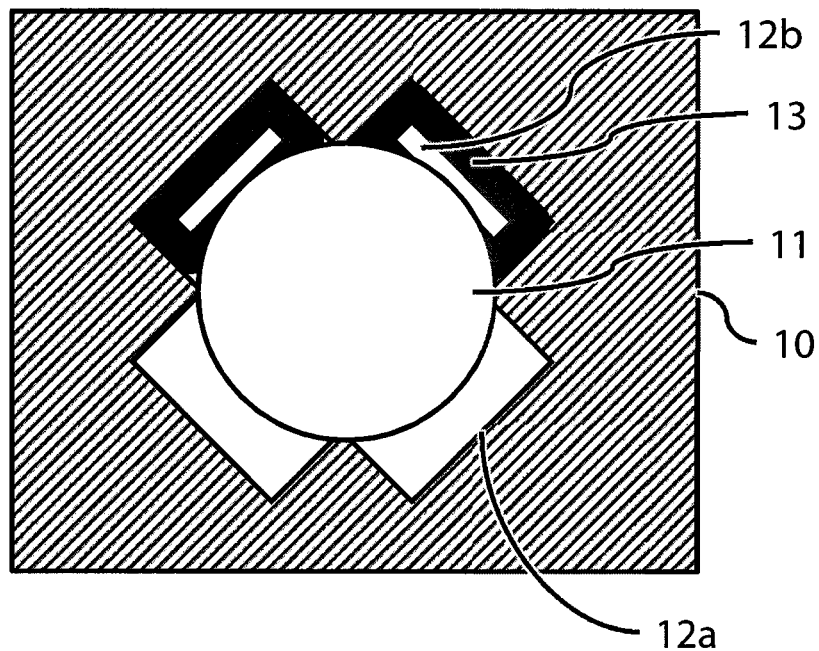
FIG. 1, already described, schematically illustrates, in top view, a foliated passage in a tube support plate, in which passes a tube, according to a standard configuration of a steam generator.
Figure 2:
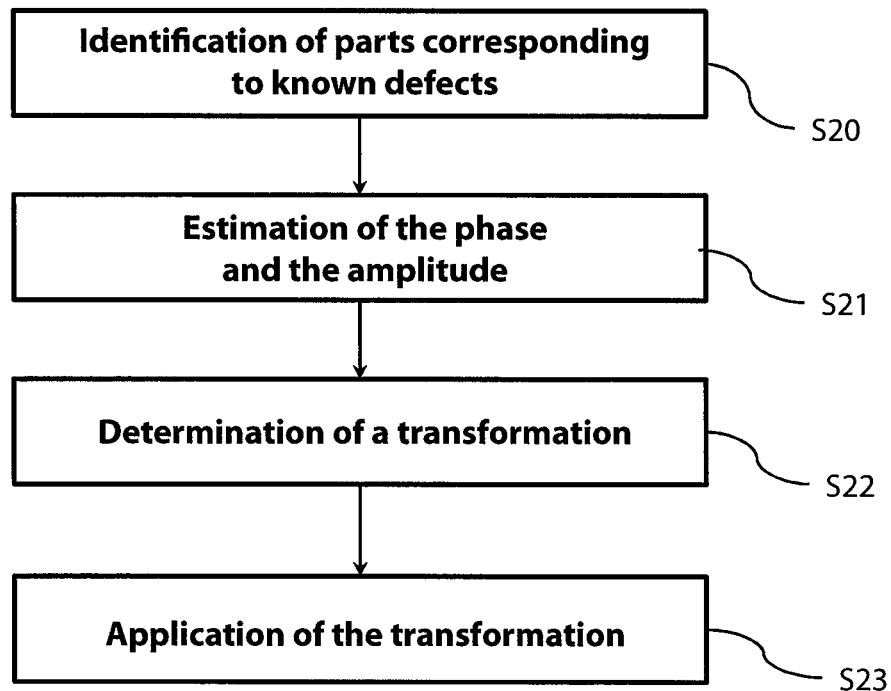
FIG. 2 is a schematic diagram illustrating the calibration of the measurement signal.
Figure 3:
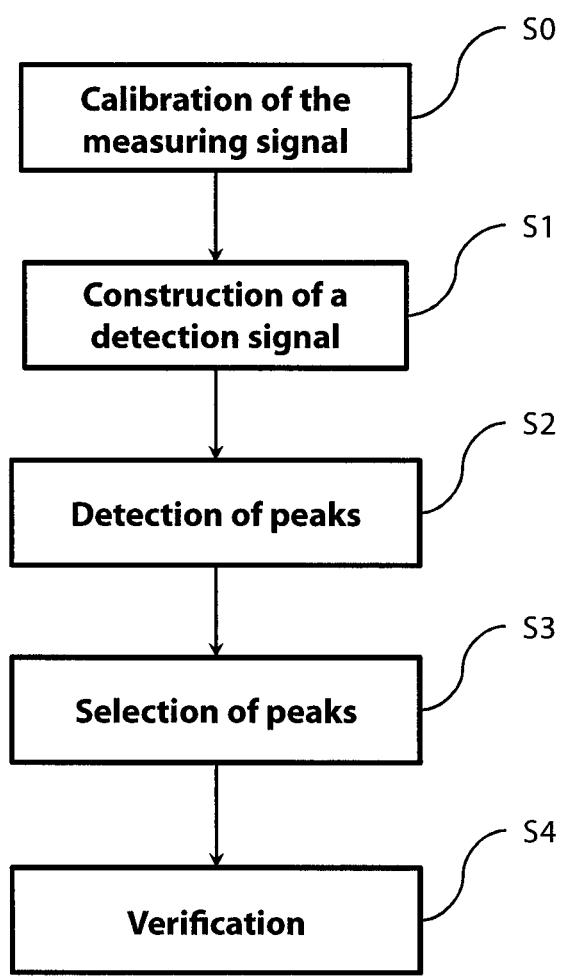
FIG. 3 is a schematic diagram of the extraction of the parts of signal corresponding to the passage of the tube support plates.
Figure 4:
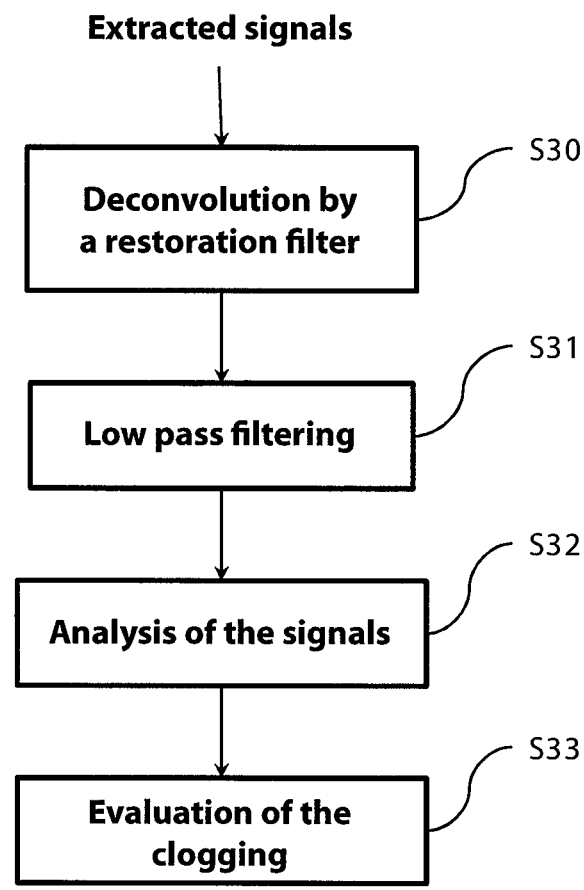
FIG. 4 is a schematic diagram of the method for evaluating the clogging.

This involves calibrating the signals with respect to reference signals, known as calibration signals. The latter correspond to defects established on the calibration tube, and the characteristics (amplitude and phase) of which are known. The calibration (step S0) takes place in the same manner whatever the acquisition frequency considered, with, in reference to FIG. 2, for each tube controlled:

- identification (step S20) of the parts of the measurement signal corresponding to known defects of the tube of the heat exchanger,
- estimation (step S21) of the phase and the amplitude of the parts of the measurement signal corresponding to the known defects,
- determination (step S22) of a transformation to apply to the measurement signal from said parts of the measurement signal corresponding to known defects to calibrate the measurement signal,
- application (step S23) of the transformation to the measurement signal.

Let $z_{untreated}(f) = x+jy$ (where j is the imaginary number) derived from an acquisition at frequency f, and $z_{calib}(f) = x_{calib}+jy_{calib}$ the complex impedance measured for a calibration defect given at the same frequency.

A calibration defect is characterised by two parameters $A_0$ and $\theta_0$ which are respectively the amplitude and the phase of the max-min vector (maximum amplitude vector on the representation according to Lissajous). These are the characteristics that the calibration defect should have after calibration.

Before calibration, these two parameters are respectively equal to A and $\theta$. The calibration of the signal z then consists in a rotation of angle $\delta\phi=\theta_0-\theta$ and a homothetic transformation of the $h=A_0/A$ parameter as described by the following equation:

$$z = h z_0 e^{j\delta\phi}$$

Actually, use is not made of the geometric configuration of the tube or the heat exchanger to detect the zone of the defect, but uniquely the characteristics of the signal (phase and amplitude). A calibration is thus available that is independent of the problems of handling the probe or sampling the signal, which are capable of falsifying the assessment of the position of the part of the signal corresponding to the defect.

Once the measurement signal has been calibrated, it remains to determine the parts of the multifrequency measurement signal corresponding to the passage at the tube support plates 10 of the eddy current detecting probe acquiring said measurement signal in the tube of the heat exchanger.

The measurement signal is very noisy and cannot be used directly to detect the tube support plates 10. In order to facilitate this detection, a detection signal, noted d[n], is constructed by linear combination of components of the measurement signal of different frequencies to minimise the energy of the detection signal between the tube support plates 10, while taking a high value at the passage of tube support plates 10.

The signals available at the input of the algorithm are the three calibrated complex signals $z_A[n]$, $z_1[n]$ and $z_3[n]$ corresponding to the return of the probe in the tube. Only the signals corresponding to the differential mode (z1 and z3), more sensitive to the probe passing by a plate, are used in this part. The respective real and imaginary components of the signal $z_i[n]$ are noted $x_i[n]$ and $y_i[n]$.

Firstly the set of available measurements is filtered by a high pass filter in order to delete the small variations of signals due to the horizontal movement of the probe in the tube. For each signal available a high pass filter (for example a Butterworth filter) is applied, for example of 0.01 reduced cut-off frequency. The signals resulting from the filtering of the signals $z_1$ and $z_3$ are noted $z_{1f}$ and $z_{3f}$. The real and imaginary parts of these signals are thus noted:

$$z_{1f}[n] = x_{1f}[n] + jy_{1f}[n]$$

$$z_{3f}[n] = x_{3f}[n] + jy_{3f}[n]$$

This first filtering operation makes it possible to construct signals having a constant and zero average base line. To then construct a detection signal that is the weakest possible between the plates, an observation window is firstly searched for expressed in number of samples of signal which limits the impact of the passage of a tube support plate 10.

To do so, information is available on the average velocity v of the probe, as well as on the sampling frequency $f_e$. Knowing the velocity of the probe and its sampling frequency, each distance may be converted into a number of signal samples according to the formula:

$$N_{sample} = \frac{distance \times f_e}{v}$$

It is possible for example to search for an observation window corresponding to a length of M samples less than the number of samples between two successive tube support plates 10 $N_{pe,pe}$, for example $$M = \frac{N_{pe,pe}}{2}.$$

This search is carried out for example on the signal $x_{3f}$, $x_{3f}$ having a high variance during the passage of the probe at a tube support plate 10. It suffices to find such a window to search for the portion of the signal of length M where the variance of $x_{3f}$ is minimal. By noting $m_0$ the first index of this window, this leads to:

$$m_0 = \underset{m}{\operatorname{argmin}} \left\{ \sum_{n=m}^{m+M-1} \left( x_{3f}[n] - \frac{1}{M} \sum_{n=m}^{m+M-1} x_{3f}[n] \right)^2 \right\}$$

However, the portions of signal corresponding to the passage by the tube support plates 10 are not known, since this is precisely what it is sought to determine. Thus, if a tube support plate 10 was found in the observation window, it could significantly impact the remainder of the method.

In order to limit the impact of the passage of a tube support plate 10 in the calculation, a sufficiently large window is preferably chosen. For example, the observation window may correspond to an estimated number of samples of the measurement signal representing the distance between consecutive tube support plates 10 along the tube 11, that is to say of size $M=N_{pe,pe}$.

In order to limit the impact of the passage by a tube support plate 10, it is also possible to choose the set of indices of the signal n such that $|x_{3f}[n]|$ is below a certain threshold. This threshold may be for example the standard deviation of the signal $x_{3f}$.

Different components of the measurement signal are then combined to determine a detection signal, the combination thereby made being chosen to minimise the energy of the detection signal. The combination of the different components of the measurement signal is an adaptive linear combination, the values of the weighting coefficients used for this combination being determined, for one sample of the detection signal, by minimisation of the variance of the detection signal on the observation window of the measurement signal around this sample.

Preferably, the different components of the measurement signal combined to determine the detection signal are real and imaginary components of the measurement signal. Similarly, different components of the measurement signal combined to determine the detection signal are components of different frequencies.

Weighting coefficients $\alpha$, $\beta$ and $\gamma$ are thus sought such that $$x_{3f}[n] \approx \alpha \cdot x_{1f}[n] + \beta \cdot y_{3f}[n] + \gamma \cdot y_{1f}[n]$$

in order to construct the detection signal d[n] defined by $$d[n] = x_{3f}[n] - \alpha \cdot x_{1f}[n] - \beta \cdot y_{3f}[n] - \gamma \cdot y_{1f}[n]$$

Furthermore, to manage the considerable non-stationarity of the components of the measurement signal, the coefficients $\alpha$, $\beta$ and $\gamma$ are updated for each signal sample. More precisely, the triplet $\{\alpha[n], \beta[n], \gamma[n]\}$ chosen at an instant n is that which minimises the power of the reconstruction error on a signal window centred on the n-th sample:

$$\{\alpha[n], \beta[n], \gamma[n]\} = \operatorname*{argmin}_{\alpha,\beta,\gamma} \left\{ \sum_{k=n-M/2}^{k=n+M/2-1} (x_{3f}[k] - \alpha x_{1f}[k] - \beta y_{3f}[k] - \gamma y_{1f}[k])^2 \right\}$$

The optimisation of $\{\alpha[n], \beta[n], \gamma[n]\}$ is carried out by means of the least squares algorithm. It will be noted that the number of coefficients may be changed.

A detection signal d[n] chosen by adaptive linear combination of real and imaginary components of the measurement signal is thereby obtained.

Such a construction of the detection signal has several advantages:
- an automatic estimation of the optimal coefficient of combination of frequencies (i.e. search for the coefficient minimising the energy of the outside of plate signal);
- the combination may take place between all the components (real and imaginary parts) of the different frequencies;
- the combination coefficients are not constant along the tube, but vary in order to adapt to the tube. Variations of the condition of the tube are thus managed.

Once the detection signal has been constructed, it remains to detect the peaks of the detection signal likely to correspond to the passage of tube support plates 10, by comparison with a detection threshold. In fact, the detection signal thereby created contains different peaks, which correspond to the probe passing the different plates, and not only the tube support plates 10, and other elements of structures.

These signal peaks may be identified by only retaining signal peaks above a detection threshold s.

Preferably, the detection threshold for detecting the peaks of the detection signal is a function of the minimum value that the standard deviation $\sigma$ of the detection signal takes over a part of the signal corresponding to a number of samples less than the estimated number of samples between two consecutive tube support plates 10.

The standard deviation $\sigma$ may be determined in the following manner:

$$\sigma = \min_m \left\{ \sqrt{\frac{1}{M-1} \sum_{n=m}^{m+M-1} \left( d[n] - \frac{1}{M} \sum_{n=m}^{m+M-1} d[n] \right)^2} \right\}$$

The detection threshold must then be a compromise between the risk of false detections (a too low threshold leads to the detection of numerous peaks not corresponding to the probe passing a tube support plate 10) and the risk of not detecting a tube support plate 10. It may for example be comprised between 5 and 15 $\sigma$, preferably 10 $\sigma$.

It may be that the probe passing a tube support plate results in several passages of the signal above the detection threshold. To only retain a single peak per plate, to then pinpoint the peaks corresponding to the tube support plates 10, the following test is carried out on successive pairs of peaks: if n1 and n2 are two indices of successive peaks, it will be said that n2 is a "secondary peak" of n1 if d[n1]>d[n2] and if the number of samples between n1 and n2 is considerably below the minimum distance estimated between two peaks of plates.

Thus, prior to the step of selection of the peaks, the peaks detected are restricted to the peaks corresponding to a local maximum of the detection signal over a range of the detection signal corresponding to a number of samples on either side of the local maximum less than or equal to the minimum of the following three values:
- 0.5 times an estimated number of samples between two tube support plates,
- 0.8 times an estimated number of samples between the tube support plate of the hot branch the closest to the cold branch of said heat exchanger and the tube support plate of the cold branch the closest to the hot branch of said heat exchanger,
- 0.8 times an estimated number of samples between a first of the tube support plates and another preceding plate in the direction of circulation of the probe.

The secondary peaks being deleted, it then remains to select the peaks of the detection signal corresponding to the passage of the tube support plates 10 by a determination of the peaks of the signal having a regular spacing.

Ideally, if the probe has a known and constant velocity v, then the number of samples between two plates is exactly proportional to the distance between plates:

$$N_{pe,pe} = \frac{\text{distance between plates} \times f_e}{v}$$

In this ideal case, it would suffice to identify the indices of the corresponding samples to only retain the peaks for which the indices are exactly spaced by $N_{pe,pe}$. In practice, the velocity of the probe is not exactly constant nor precisely known and may vary along the tube. The gap between two peaks corresponding to tube support plates 10 is thus not exactly equal to $N_{pe,pe}$ and it may be different from one pair of tube support plates 10 to another. This average gap between tube support plates 10 may however be estimated.

To do so, the peaks of the detection signal corresponding to the passage of the tube support plates 10 are selected by the selection of at least one sub-set of peaks minimising the difference between the number of samples of the detection signal between two successive peaks of said sub-set and a median value of the number of samples of the detection signal between two successive peaks.

A tube of a heat exchanger extends along it through two parts, generally designated cold branch and hot branch, according to the direction of flow of the fluids realising the heat exchange, separated by a structure without tube support plate 10 designated as the curve. Consequently, such a structure breaks the regularity of the spacing of the tube support plates. It suffices to call on the following method for one branch, then for the other, to select all of the peaks corresponding to the tube support plates 10.

$i_k$ designates the index of the k-th peak detected, $\Delta[k]=i_{k+1}-i_k$ the gap between the successive peaks k and k+1, and $N_{pe,pe,real}$ the average number of samples between two tube support plates 10. Since the tube support plates are the majority plates along the tube, the majority of the values taken by $\Delta[k]$ is situated around $N_{pe,pe,real}$. An estimation of $N_{pe,pe,real}$ is thus provided by the median value of the set of values taken by $\Delta[k]$:

$$N_{pe,pe,real} = \text{median}\{\Delta[k]\}$$

It then remains to find, among the set I of peak indices, the sub-set $I_{peak}$ of indices corresponding to the number of tube support plates NbPe, such that the gaps between two successive indices are always more or less equal to $N_{pe,pe,real}$:

$$I_{peak} = \operatorname*{argmin}_{I} \sum_{i \in I} (\Delta[i] - N_{pe,pe,real})^2.$$

The indices of samples of the signal corresponding to the passage of tube support plates 10 are thus obtained.

Once the set of indices corresponding to the probe passing the tube support plates 10 has been estimated, it is then possible to carry out at a subsequent step of verification in which the positions of the peaks of the detection signal corresponding to the passage of the tube support plates 10 are compared with known data on the geometry of the heat exchanger. Two criteria are used: the length of the tube support plates 10 and the length of the curve.

The first verification criterion relates to the length of the curve: for each tube, the number of samples between the final plate of the hot branch and the final plate of the cold branch is compared to the known distance according to the plans. A margin is allowed, in order to take account of the uncertainty on the velocity of the probe.

The second validation criterion makes it possible to verify the length of the set of plates detected. The detection algorithm having made it possible to estimate the indices of the tube support plates 10 uses the positive peaks of the detection signal. However the probe passing a tube support plate 10 generates on the signal at least one positive peak and one negative peak (the two peaks correspond to the probe passing the edges of plates).

A new estimation of the indices of the tube support plates 10 may thus be obtained by detecting this time the negative peaks of the detection signal, without taking into account the first peaks detected. In practice, it suffices to recall the detection algorithm of the peaks by taking the opposite of the detection signal (d[n] becomes −d[n]). The method may thus comprise a final step of verification in which the opposite of the detection signal is taken, the steps of detection S2 and of selection S3 of the positions of the peaks of the detection signal corresponding to the passage of the tube support plates 10 are applied and a check is made that the gaps between the positions of the peaks on the detection signal and on its opposite correspond to the edge to edge distance of a tube support plate 10.

Two sets of estimated indices are then thus available, for each branch. If these two sets of indices are correct, the difference between the two estimations of a same tube support plate 10 must be of the order of magnitude of the size of a tube support plate 10. Taking account of imprecisions on the velocity of the probe and plate edge effects, a margin is allowed to validate the estimation.

Since the positions of the tube support plates are known in the measurement signal, it is thus possible to extract therefrom the useful parts relative to the probe passing the tube support plates.

Evaluation of the Clogging

The useful signal relative to the passage of the tube support plates 10 is thus available after its extraction from the set of the measurement signals emitted by the SAX probe. To do so, methods other than that described previously may be envisaged. At this stage, for each tube support plate 10, a signal corresponding to the probe passing the downstream edge of the tube support plate 10, and a signal corresponding to the probe passing the upstream edge of the tube support plate 10 has thus been extracted from the measurement signal.

A lower edge signal corresponding to the probe passing the downstream edge of the tube support plate 10, and an upper edge signal corresponding to the probe passing the upstream edge of the tube support plate 10 are then determined from the measurement signal.

Thus, as explained above, the probe acquires at least in part the measurement signal in differential mode, and the measurement signal is a multifrequency signal composed of at least two signals at different frequencies.

Preferably, only signals corresponding to the differential mode ($z_1$ and $z_3$) are used because they are more sensitive to the passage of the tube support plate 10. These signals are acquired at different frequencies, and the lower edge signal is determined as the linear combination of at least two signals at frequencies different to said measurement signal, in this instance $z_1$ and $z_3$.

This linear combination involves a complex $\alpha$ coefficient optimised to minimise the signal power along the tube 11 outside of the tube support plate zones 10.

Thus, the lower edge signal $z_{low}$ is determined from the signals obtained in differential mode over the frequencies f3 and f1, such that $$z_{low}[n] = z_{3low}[n] - \alpha \cdot z_{1low}[n],$$

with $\alpha = \operatorname{argmin}\|z_3[n] - \alpha \times z_1[n]\|^2$, for the indices n corresponding to the signal outside of the tube support plate zones 10, and $z_{3low}$ corresponding to the response of the probe in differential mode on the frequency f3 during the probe passing the downstream, that is to say lower, edge of the tube support plate 10, and $z_{1low}$ corresponding to the response of the probe in differential mode on the frequency f1 during the probe passing the downstream, that is to say lower, edge of the tube support plate 10.

The same is done with the upper edge signal, with preferably the same coefficient α, such that $z_{upp}[n]=z_{3upp}[n]-\alpha \cdot z_{1upp}[n]$, with $z_{3upp}$ corresponding to the response of the probe in differential mode on the frequency f3 during the probe passing the upstream, that is to say upper, edge of the tube support plate 10, and $z_{1upp}$ corresponding to the response of the probe in differential mode on the frequency f1 during the probe passing the upstream, that is to say upper, edge of the tube support plate 10.

Two complex signals are thus obtained. The lower edge signal $z_{low}$ may be expressed as:

$$z_{low}[n]=x_{low}[n]+i \cdot y_{low}[n]$$

with $x_{low}$ and $y_{low}$ respectively the real and imaginary components of the lower edge signal and i the imaginary unit such that $i^2=1$. Similarly, the upper edge signal $z_{upp}$ may be expressed as:

$$z_{upp}[n]=x_{upp}[n]+i \cdot y_{upp}[n]$$

with $x_{upp}$ and $y_{upp}$ respectively the real and imaginary components of the upper edge signal and i the imaginary unit such that $i^2=1$.

It thus remains to implement an appropriate processing of these signals in order to evaluate the clogging of the passage of the tube support plate 10. This processing is implemented on the lower edge signal, which is a complex signal. In fact, the clogging of the foliated passages, that is to say the lobes 12a, 12b, in the tube support plates 10 takes place at the lower edge of the tube support plates 10, upstream of the passage for the flux of fluid passing through the tube support plate 10. It is thus from the lower edge signal that the level of clogging may be estimated.

More precisely, the lower edge signal is deconvolved by the complex impulse response of the probe.

Actually, in an ideal case of a perfect SAX probe, the signal should only contain a series of complex impulses, corresponding to the passage by an edge of tube support plate 10, on meeting a deposition, and the study of the single lower edge signal should be sufficient to quantify the clogging.

However, in practice, the response of the SAX probe to an impedance variation is not perfect. It is known as the impulse response of the probe. It is thus necessary to restore the lower edge signal to recover the response of the probe representative of the clogging state of the foliated passage in the tube support plate 10. To this end an impulse response estimation of the probe is determined, preferably corresponding to the probe passing a clean edge of the tube support plate 10 in the tube 11, for example from the upper edge signal. It is then sought to deconvolve the lower edge signal $z_{low}[n]$ by a signal h[n] corresponding to the impulse response of the probe at the passage of the tube support plate.

To do so, it is possible to use a filter. Such a filter is designated deconvolution filter or instead restoration filter. The deconvolution filter is calculated from the impulse response estimation, and the lower edge signal is deconvolved by means of said deconvolution filter (step S30). The deconvolution filter may be an approximation of the inverse of the impulse response of the probe. It may also be a Wiener filter and the deconvolution may thus be a Wiener deconvolution, which constitutes a preferential embodiment of the method described. Other deconvolution methods exist and may be used.

For example, the deconvolved lower edge signal $z_{low,id}[n]$ that best corresponds to the lower edge signal $z_{low}[n]$ that has been observed may be searched for:

$$z_{inf,id}[n]=\mathrm{argmin}_{z[n]}\{J_1(z_{inf}[n]-z[n]\oplus h[n])+\lambda \times J_2(z[n])\}$$

with $J_1$ the data fit criterion (for example an $L_2$ norm, a squared $L_2$ norm, an $L_1$ norm, etc.) and $J_2$ a criterion reflecting a characteristic a priori known on the signal that it is sought to reconstruct (for example an $L_2$ norm, a squared $L_2$ norm, an $L_1$ norm, a function of the gaps between neighbouring samples z[n]−z[n−1]). The term λ makes it possible to accord more or less importance to the a priori on the solution ($J_2$) compared to the data fit ($J_1$). This criterion may also be written in the frequency domain.

There are thus several variants of deconvolution criteria J1 and J2 that may be used, and, for each variant, several resolution methods, for example by filtering or by optimisation methods.

In the case where the deconvolution filter is a Wiener filter, the frequency response of the Wiener filter is of the form:

$$G[f] = \frac{H^*[f]}{\|H[f]\|^2 + \frac{B[f]}{S[f]}}$$

with the exponent * designating the complex conjugation, H[f] the Fourier transform of the impulse response of the probe, S[f] the power spectral density of the signal to be estimated and B[f] the power spectral density of the noise. A zero-padding, that is to say an addition of zeros within the signals, may be carried out during the calculation of the discrete Fourier transforms in order to increase the frequency resolution.

The impulse response h[n] of the probe may be estimated from the response of the probe at the passage of the upstream edge of the tube support plate 10 by the probe, that is to say by means of the upper edge signal, according to the formula:

$$h[n]=-z_{upp}[-n].$$

For example, from processing operations carried out to extract the useful parts of the measurement signal, the indices $i_{low}$ and $i_{upp}$ of the measurement signal corresponding respectively to the passages of the lower and upper edges of the tube support plate 10 are known. For a sampling frequency Fe=1000 Hz, a velocity of the probe v=0.5 m·s$^{-1}$ and a length of tube support plate 10 of 30 mm, there are 60 samples of signal corresponding to the tube support plate 10, and an impulse response of around 20 samples. It is then possible to choose for the range of values of the upper edge signal $z_{upp}[n]$ the 60 samples following the centre of the tube support plate 10 determined at around 0.5×($i_{low}+i_{upp}$), i.e. a margin of 20 samples on each side of the impulse response. These figures are obviously indicated as a non-limiting example of the use of the upper edge signal $z_{upp}[n]$ for the impulse response estimation of the probe.

Several approaches are possible for estimating the signal to noise ratio corresponding to the ratio of the power spectral density of the noise B[f] and the power spectral density S[f] of the signal to be estimated. One of these approaches consists in approximating this ratio by a constant. In fact, the signal to be estimated corresponds to an ideal lower edge signal which would show a series of impulses corresponding to the variations of complex impedance encountered by the probe in the vicinity of the tower edge of the tube support plate 10. Consequently, the power spectral density S[f] of this signal may be considered as a constant. The power spectral density of the noise B[f] may be determined on the portions of the signal between the tube support plates 10. This may be assimilated with a white noise, and thus this power spectral density of the noise B[f] may be considered as a constant. Thus the ratio of the power spectral densities of the noise and of the signal to be estimated may be considered as a constant. This constant may be adjusted empirically, by taking for example:

$$\frac{B[f]}{S[f]} = 10 \times \sigma^2,$$

with $\sigma^2$ the power of the noise, calculated on an out of plate zone.

Once the deconvolution filter has been determined, it is then possible to carry out the deconvolution of the lower edge signal by means of said deconvolution filter. The deconvolution filter g is then applied to the lower edge signal $z_{low}$ to obtain a complex deconvolved lower edge signal $z_{low\ id}$ introduced by the impulse response of the probe:

$$z_{low\ id} = z_{low} * g.$$

In practice, this operation may be carried out in the frequency domain:

$$z_{low\ id} = TF^{-1}\{Z_{low}[f] \times G[f]\},$$

with $Z_{low}[f]$ the Fourier transform of the lower edge signal $z_{low}$, G[f] the Fourier transform of the deconvolution filter g, and $TF^{-1}$ indicating the inverse Fourier transformation.

In order to avoid amplifying too substantially certain frequencies only corresponding to the measurement noise, a filtering (step S31) by a low pass filter is applied to the deconvolved lower edge signal, the cut-off frequency of said low pass filter being determined by means of a standard deviation of a Gaussian function constituting an approximation of the real part of an impulse of the lower edge signal corresponding to the passage of an edge of tube support plate 10.

In fact, the real or imaginary part of an impulse of the lower edge signal corresponding to the passage of an edge of tube support plate 10 has forms very similar to Gaussian functions or derivatives thereof. For example, it is possible to assimilate to a Gaussian function the impulse 0 in the real part of the lower edge signal corresponding to the passage of the lower edge of the tube support plate 10 in a configuration without clogging, and to a linear combination of derivatives of the Gaussian function the impulses in the imaginary part of the lower edge signal corresponding to the passage of the lower edge of the tube support plate 10 in a clogged configuration.

If $\sigma$ is the standard deviation of this Gaussian function, generally of the order of 3 or 4 samples, the Fourier transforms of the signals to be deconvolved no longer contain energy above a maximum frequency $f_{max}$:

$$f_{max} = \frac{3}{2\pi\sigma}.$$

This maximum frequency $f_{max}$ may thus be chosen as cut-off frequency of the low pass filter.

Once the deconvolved lower edge signal thereby filtered, it remains to analyse said signal to evaluate the clogging. This analysis is preferably based on the analysis of the profile of the real part and the imaginary part of the lower edge signal. These profiles are compared to the ideal profiles expected for several configurations in order to identify the configuration to which the deconvolved lower edge signal corresponds. Several examples are given hereafter, for the case of a probe entering via the lower edge of the plate. The same configurations would be obtained in the case of a probe exiting via the lower edge of the plate.

Figure 5:
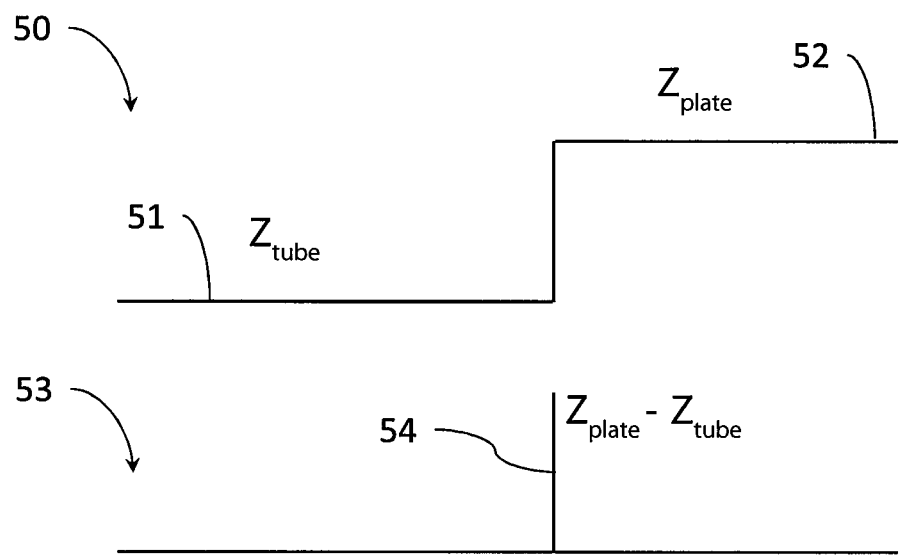
FIG. 5 illustrates the changes of impedance recorded by an ideal probe in a non-clogged passage configuration (so-called clean plate)

The ideal temporal response of the probe passing through a clean edge of a tube support plate 10, that is to say free of clogging or fouling, is illustrated by FIG. 5. In this figure, the curve 50 represents the complex impedance in absolute mode during the passage of an edge of a clean tube support plate 10. This comprises a first part 51 corresponding to an impedance characteristic of the tube 11 in the absence of tube support plate 10, noted $Z_{tube}$, and a second part 52 corresponding to an impedance characteristic of the presence of the plate $Z_{plate}$.

Curve 53 represents the complex impedance in differential mode during the passage of an edge of a clean tube support plate 10, in correspondence with curve 50. The passage of the rim of tube support plate 10 results in an impulse 54 characteristic of the passage of the impedance from the tube 11 to that of the tube support plate 10, and corresponding to $Z_{plate} - Z_{tube}$.

Figure 6:
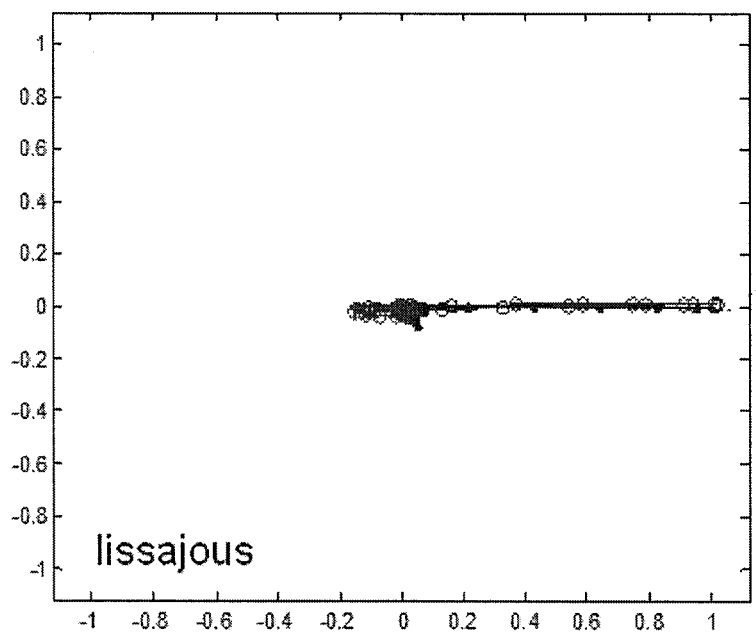

FIG. 6 shows the Lissajous signal, with the real part of the deconvolved lower edge signal on the X-axis and the imaginary part on the Y-axis. FIG. 7 shows in a temporal manner, at the top the real part of the deconvolved lower edge signal, and at the bottom the imaginary part of the deconvolved lower edge signal. The deconvolved upper edge signal is also represented, this being considered as reference representing a clean edge of a tube support plate 10. However, in these figures, the lower edge signal and the upper edge signal are superimposed, indicating that the lower, or downstream, plate edge is clean, in the same way as the edge of the upper plate.

FIGS. 8 to 11 illustrate a configuration in which the lower plate edge is clogged by a deposition of magnetite situated at the same level as the lower plate edge.

The ideal temporal response of the probe passing through a clogged edge of a tube support plate 10 is illustrated by FIG. 8. In this figure, curve 80 represents the complex impedance in absolute mode during the passage of a clogged edge of a tube support plate 10. This comprises a first part 81 corresponding to an impedance characteristic of the tube 11 in the absence of tube support plate 10 and clogging, noted $Z_{tube}$, a second part 82 corresponding to an impedance characteristic of the presence of clogging of magnetite between the tube 11 and the tube support plate 10, noted $Z_{magn}$, and a third part 83 corresponding to an impedance characteristic of the presence of the tube support plate 10 without magnetite, noted $Z_{plate}$.

Curve 84 represents the complex impedance in differential mode during the passage of an edge of a clogged tube support plate 10, in correspondence with curve 80. The start of clogging of magnetite results in a first impulse 85 characteristic of the passage of the impedance from the tube to that of the deposition of magnetite, and corresponding to $Z_{magn} - Z_{tube}$. The end of the deposition of magnetite results in a second impulse 86 characteristic of the passage of the impedance from the deposition of magnetite to that of the plate and corresponding to $Z_{plate}$-$Z_{magn}$.

FIG. 9 shows a representation in Lissajous that an ideal signal representative of clogging should show. It shows a first signature 95 characteristic of the passage of the impedance from the tube to that of the deposition of magnetite, and corresponding to $Z_{magn}$-$Z_{tube}$. It also shows a second signature 96 characteristic of the passage of the impedance from the deposition of magnetite to that of the plate and corresponding to $Z_{plate}$-$Z_{magn}$.

The dotted line signature 97 corresponds to the signature of the passage characteristic of the passage of the impedance from the tube to that of the tube support plate in the absence of clogging, and corresponding to $Z_{plate}$-$Z_{tube}$. It will moreover be noted that the sum of the first signature 95 and the second signature 96 corresponds to the dotted line signature 97. In fact, $Z_{magn}$-$Z_{tube}$+$Z_{plate}$-$Z_{magn}$=$Z_{plate}$-$Z_{tube}$.

Figure 10:
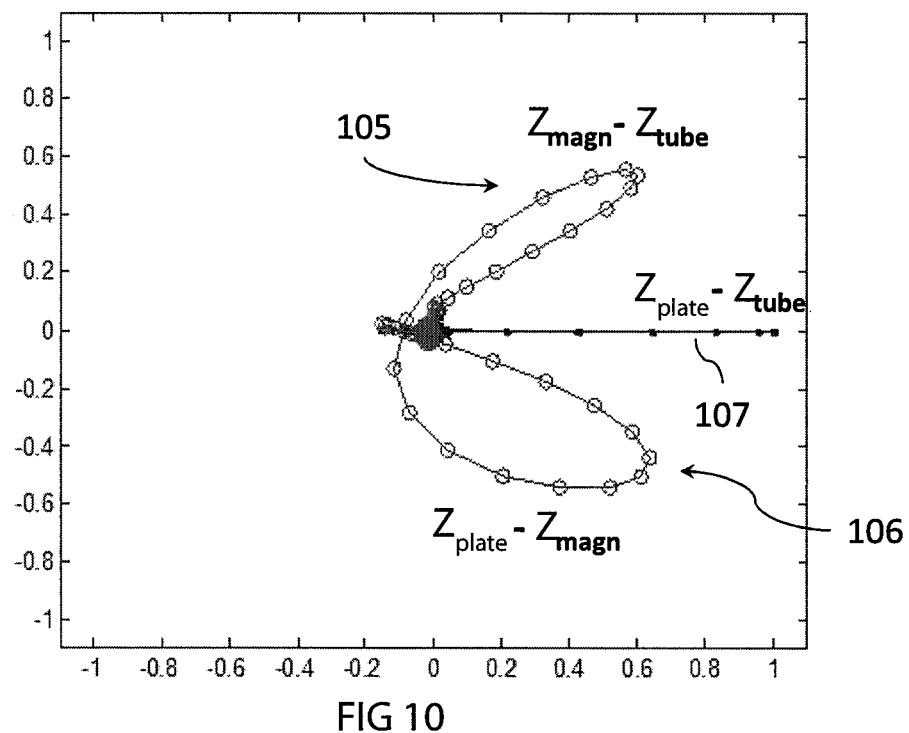
FIGS. 10 and 11 illustrate the profile of the deconvolved signals in the configuration of passage clogged by a deposition of magnetite situated at the same level as the lower edge of the tube support plate.
Figure 11:
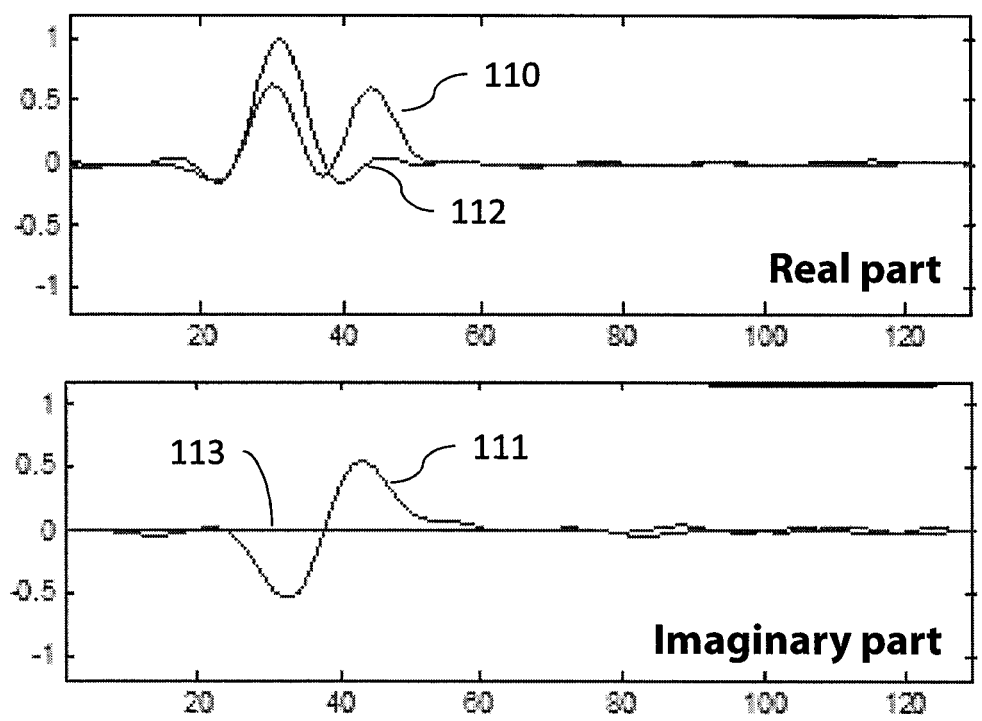

FIGS. 10 and 11 illustrate the deconvolved lower edge signal in the case of clogging by a deposition of magnetite. FIG. 10 shows a representation in Lissajous of this deconvolved lower edge signal. It shows a first signature 105 characteristic of the passage of the impedance from the tube to that of the deposition of magnetite, and corresponding to $Z_{magn}$-$Z_{tube}$. It also shows a second signature 106 characteristic of the passage of the impedance from the deposition of magnetite to that of the plate and corresponding to $Z_{plate}$-$Z_{magn}$. The third signature 107 corresponds to the signature of the deconvolved upper edge signal, assumed clean.

A very good correlation is observed between the profile of the deconvolved lower edge signal and the profile of an ideal signal. Consequently, it is easy to deduce the clogging state of the foliated passage from the deconvolved lower edge signal.

FIG. 11 shows in a temporal manner, at the top the real part of the deconvolved lower edge signal 110, and at the bottom the imaginary part of the deconvolved lower edge signal 111, in the same configuration. The real part 112 and the imaginary part 113 of the deconvolved upper edge signal are also represented, the upper edge signal being considered as reference representing a clean edge of a plate.

It may be deduced from FIGS. 10 and 11 that the lower edge signal, after deconvolution, indeed contains two complex impulses, which represent the two variations of impedance corresponding to the probe passing by the ends of the deposition clogging the foliated passage.

FIGS. 12 to 15 illustrate a configuration in which a deposition formed of a ring of magnetite is present on the tube, below the lower edge of the tube support plate.

Figure 12:
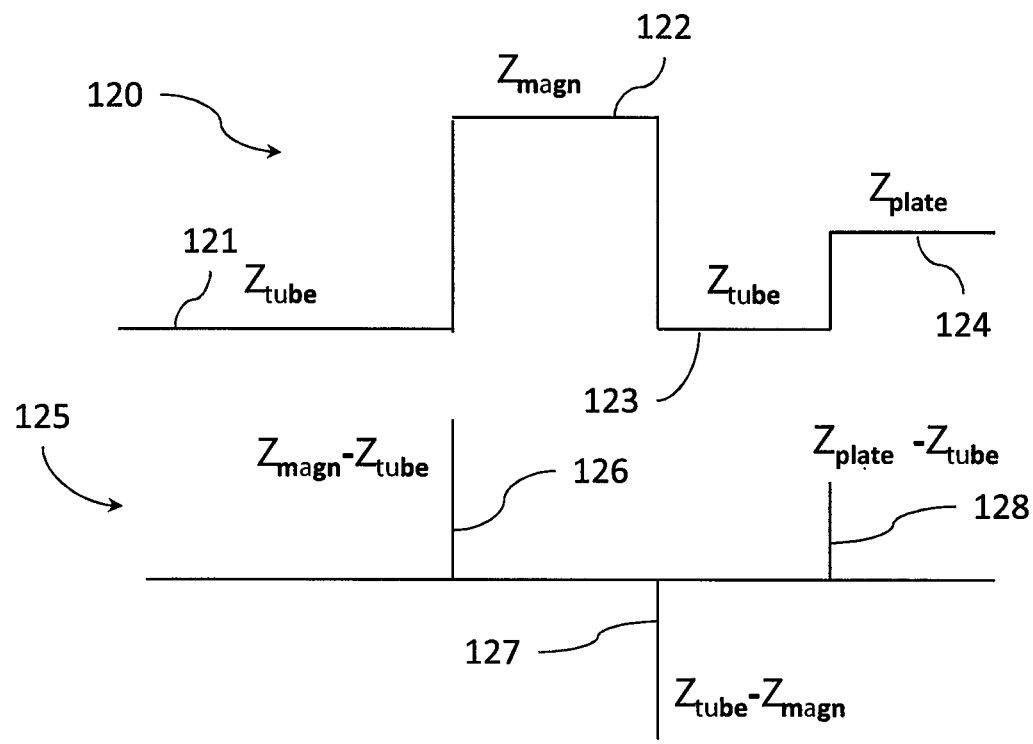
FIGS. 12 and 13 illustrate the changes of impedance plotted by an ideal probe in a configuration in which a magnetite deposition ring is present on the tube at a height below the height of the tube support plate.

The ideal temporal response of the probe in the vicinity of this ring of magnetite and this edge of tube support plate is illustrated by FIG. 12. In this figure, curve 120 represents the complex impedance in absolute mode. This comprises a first part 121 corresponding to an impedance characteristic of the tube in the absence of tube support plate and clogging, noted $Z_{tube}$, a second part 122 corresponding to an impedance characteristic of the presence of a ring of magnetite along the tube, noted $Z_{magn}$, a third part 123 corresponding to the part of the tube between the deposition and the plate, and the impedance of which is $Z_{tube}$, and finally a fourth part 124 corresponding to an impedance characteristic of the presence of the tube support plate 10 without magnetite, noted $Z_{plate}$.

Curve 125 represents the complex impedance in differential mode during the probe passing in the vicinity of this ring of magnetite and this edge of tube support plate, in correspondence with curve 120. The start of deposition of magnetite results in a first impulse 126 characteristic of the passage of the impedance from the tube to that of the deposition of magnetite, and corresponding to $Z_{magn}$-$Z_{tube}$. The end of deposition of magnetite results in a second impulse 127 characteristic of the passage of the impedance from the deposition of magnetite to that of the tube, and corresponding to $Z_{tube}$-$Z_{magn}$. The rim of the tube support plate results in a third impulse 128 characteristic of the passage of the impedance from the tube to that of the tube support plate, and corresponding to $Z_{plate}$-$Z_{tube}$.

Figure 13:
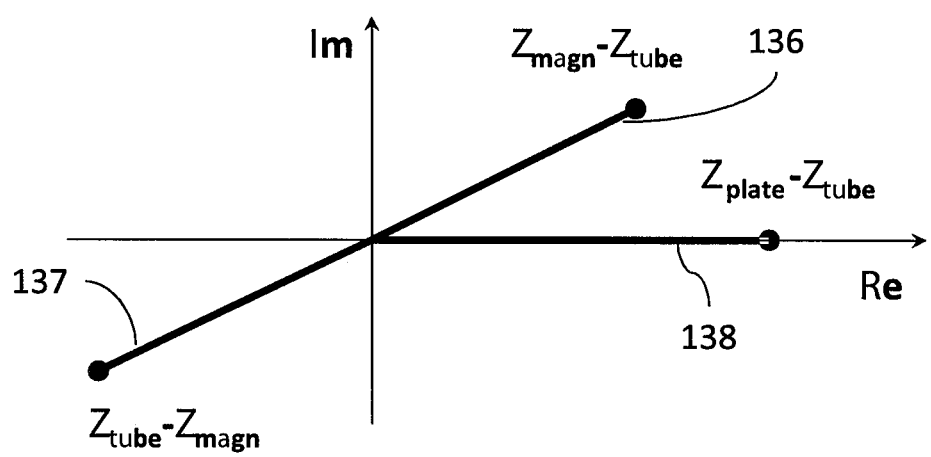

FIG. 13 shows a representation in Lissajous that an ideal signal representative of this configuration should show. It shows a first signature 136 characteristic of the passage of the impedance from the tube to that of the magnetite deposition ring, and corresponding to $Z_{magn}$-$Z_{tube}$. It also shows a second signature 137 characteristic of the passage of the impedance from the magnetite deposition to that of the tube, and corresponding to $Z_{tube}$-$Z_{magn}$. It should be noted that, logically, the second signature 137 is the opposite of the first signature 136. Finally it shows a third signature 138 characteristic of the passage of the impedance from the tube to that of the plate, and corresponding to $Z_{plate}$-$Z_{tube}$.

Figure 14:
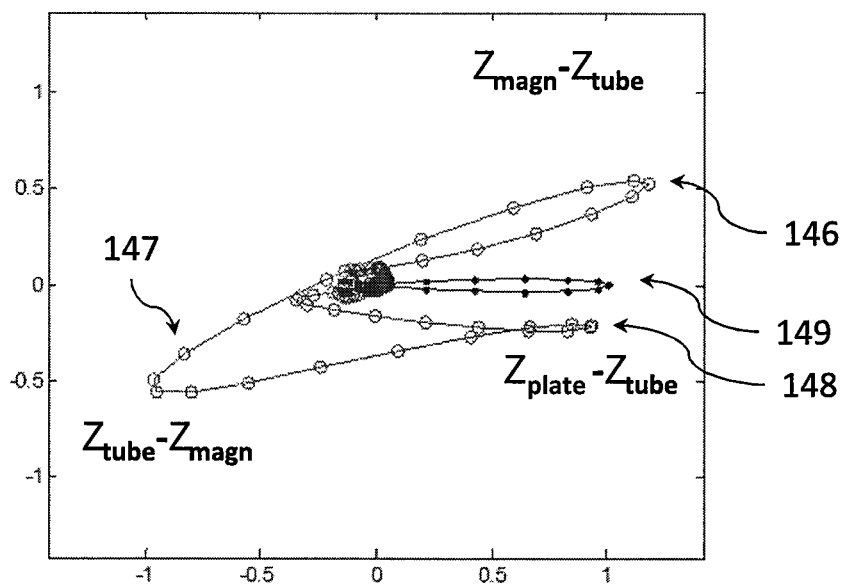
FIGS. 14 and 15 illustrate the profile of the deconvolved signals in the configuration in which a magnetite deposition ring is present on the tube at a height below the height of the lower edge of the tube support plate.
Figure 15:
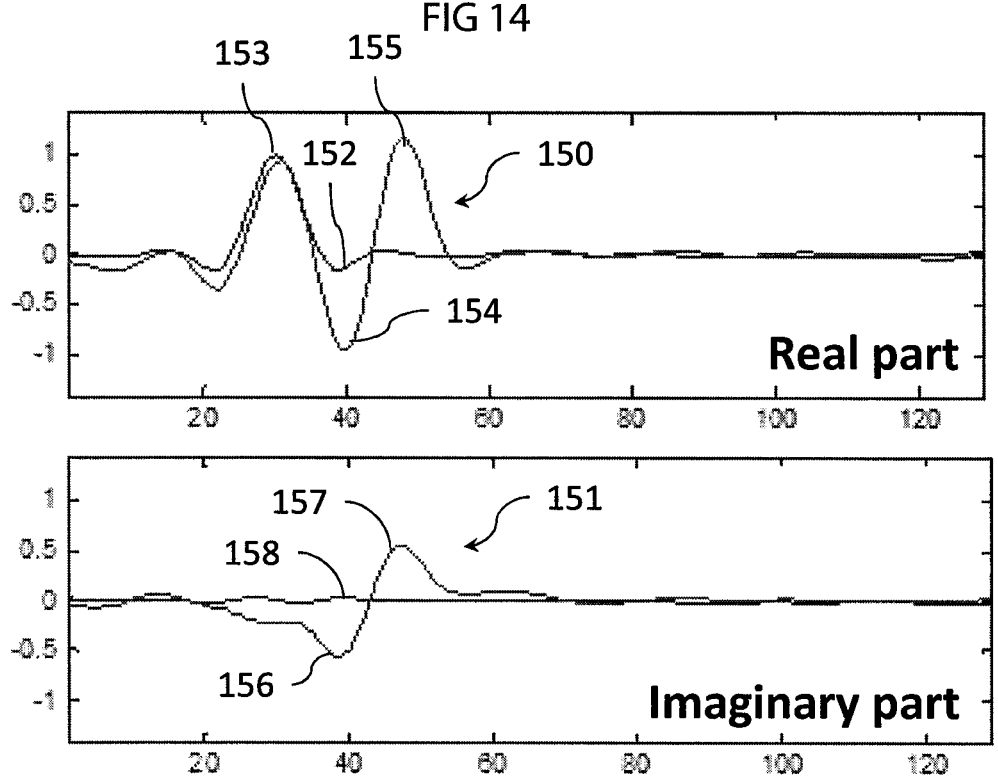

FIGS. 14 and 15 illustrate the deconvolved lower edge signal in the configuration with a magnetite deposition ring. FIG. 14 shows a representation in Lissajous of this deconvolved lower edge signal. It shows a first signature 146 characteristic of the passage of the impedance from the tube to that of the magnetite deposition ring, and corresponding to $Z_{magn}$-$Z_{tube}$. It also shows a second signature 147 characteristic of the passage of the impedance from the magnetite deposition to that of the tube, and corresponding to $Z_{tube}$-$Z_{magn}$. It should be noted that logically, the second signature 147 is the opposite of the first signature 146. Thus, two peaks are observed, that is to say signatures, of zero sum with a considerable energy on the imaginary part.

Finally it shows a third signature 148 characteristic of the passage of the impedance from the tube to that of the plate, and corresponding to $Z_{plate}$-$Z_{tube}$. The fourth signature 149 corresponds to the signature of the deconvolved upper edge signal, assumed clean. It may here be noted that the proximity of the ring of magnetite with the lower edge of the tube support plate leads to a mixture between the second signature 147 and the third signature 148.

A very good correlation is observed between the profile of the deconvolved lower edge signal and the profile of an ideal signal. Consequently, it is easy to deduce from the deconvolved lower edge signal the configuration of the clogging of the foliated passage.

FIG. 15 shows in a temporal manner, at the top the real part of the deconvolved lower edge signal 150, and at the bottom the imaginary part of the deconvolved lower edge signal 151, in the same configuration. The real part 152 and the imaginary part 158 of the deconvolved upper edge signal are also represented, the upper edge signal being considered as reference representing a clean edge of a plate.

It shows for the real part of the deconvolved lower edge signal a peak 153 corresponding to the passage of clean plate, and two peaks 154, 155, of zero sum, revealing the presence of the ring of magnetite. Two corresponding peaks 156, 157 for the imaginary part of the deconvolved lower edge signal are reproduced. The expected absence of peak corresponding to the passage from the edge of clean plate should be noted for the imaginary part.

FIGS. 16 to 19 illustrate a configuration in which a tube fouled over this length by a deposition of magnetite has a fouling break below the lower edge of the tube support plate.

Figure 16:
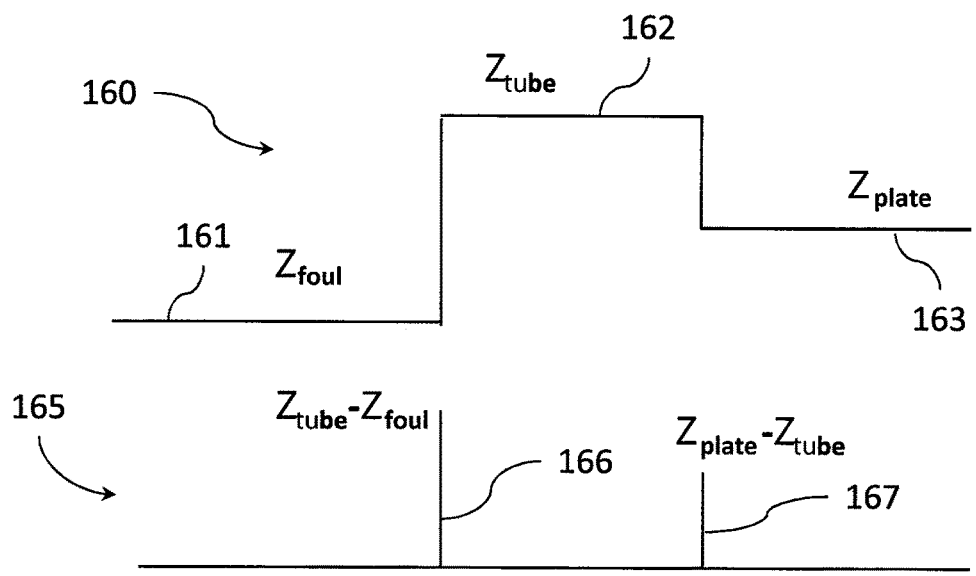
FIGS. 16 and 17 illustrate the changes of impedance plotted by an ideal probe in a configuration in which a tube fouled by a deposition of magnetite has a fouling break below the lower edge of the tube support plate.

The ideal temporal response of the probe in the vicinity of this fouling break and this edge of tube support plate is illustrated by FIG. 16. In this figure, curve 160 represents the complex impedance in absolute mode. This comprises a first part 161 corresponding to an impedance characteristic of the tube fouled by magnetite, noted $Z_{foul}$, a second part 162 corresponding to an impedance characteristic of the tube in the absence of magnetite, noted $Z_{tube}$, at the break of the fouling of the tube, and a third part 163 to an impedance characteristic of the presence of the tube support plate 10 without magnetite, noted $Z_{plate}$.

The curve 165 represents the complex impedance in differential mode during the probe passing from this fouling break and the edge of tube support plate, in correspondence with curve 160. The fouling break by the magnetite results in a first impulse 166 characteristic of the passage of the impedance from the fouled tube to that of the tube free of magnetite, and corresponding to $Z_{tube}-Z_{foul}$. The passage of the rim of the tube support plate results in a second impulse 167 characteristic of the passage of the impedance from the tube to that of the tube support plate, and corresponding to $Z_{plate}-Z_{tube}$.

Figure 17:
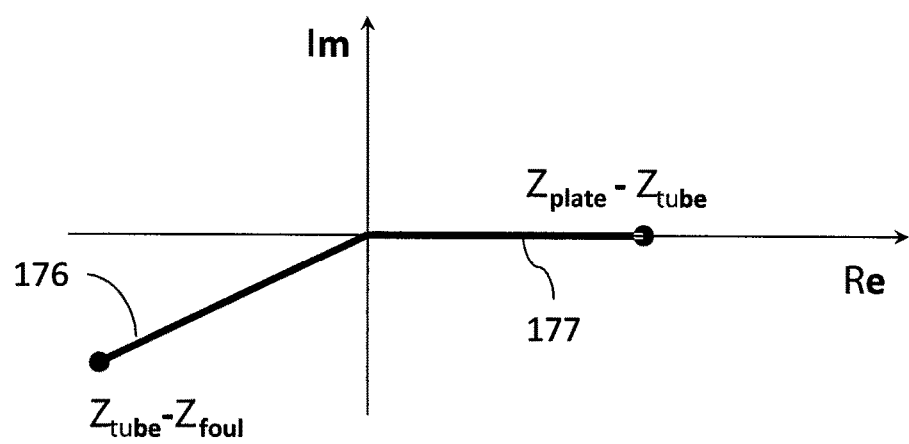

FIG. 17 shows a representation in Lissajous that an ideal signal representative of this configuration should show. It shows a first signature 176 characteristic of the passage of the impedance from the fouled tube to that of the tube free of magnetite, and corresponding to $Z_{tube}-Z_{foul}$. It also shows a second signature 177 characteristic of the passage of the impedance from the tube to that of the plate, and corresponding to $Z_{plate}-Z_{tube}$.

Figure 18:
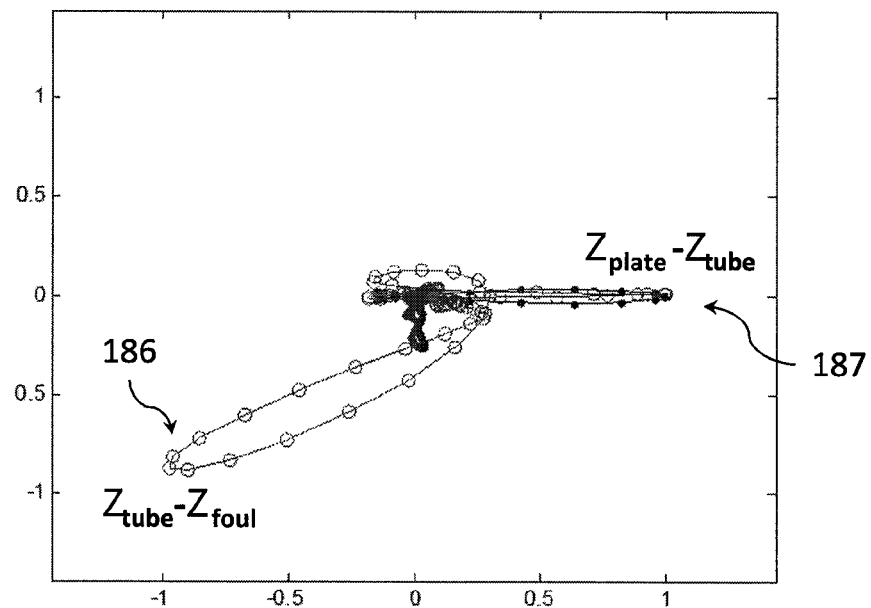
FIGS. 18 and 19 illustrate the profile of the deconvolved signals in the configuration in which a tube fouled by a deposition of magnetite has a fouling break below the lower edge of the tube support plate.
Figure 19:
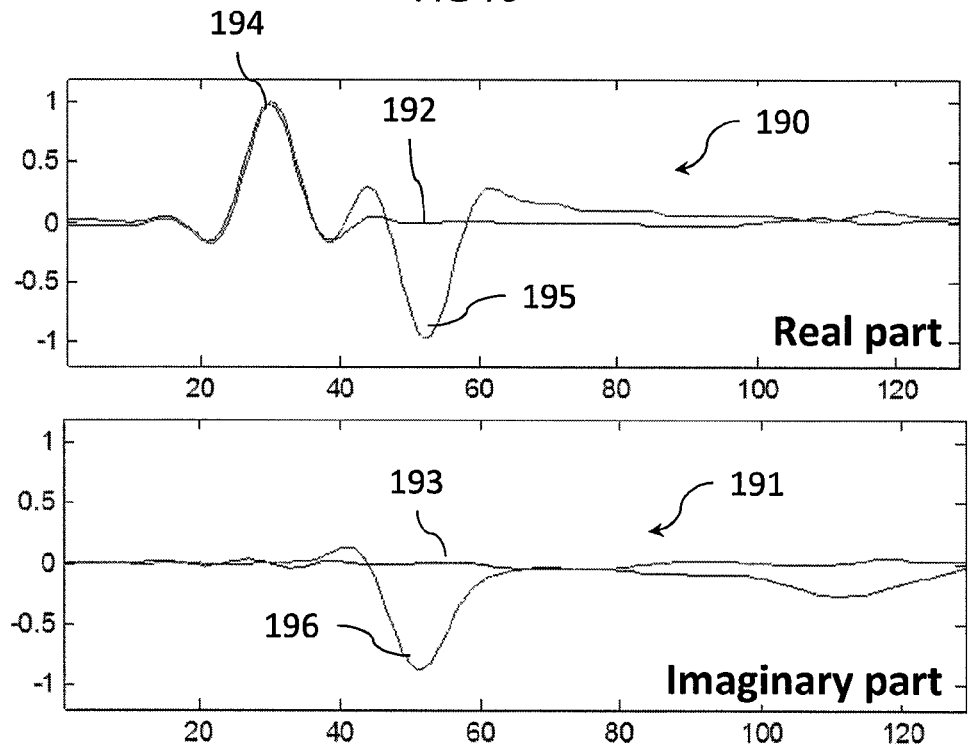

FIGS. 18 and 19 illustrate the deconvolved lower edge signal in the configuration of the tube with a fouling break. FIG. 18 shows a representation in Lissajous of this deconvolved lower edge signal. It shows a first signature 186 characteristic of the passage of the impedance from the fouled tube to that of the tube free of magnetite, and corresponding to $Z_{tube}-Z_{foul}$. It also shows a second signature 187 characteristic of the passage of the impedance from the tube to that of the plate, and corresponding to $Z_{plate}-Z_{tube}$.

A very good correlation is observed between the profile of the deconvolved lower edge signal and the profile of an ideal signal. Consequently, it is easy to deduce from the deconvolved lower edge signal the presence of a fouling break of the tube.

FIG. 19 shows in a temporal manner, at the top the real part of the deconvolved lower edge signal 190, and at the bottom the imaginary part of the deconvolved lower edge signal 191, in the same configuration. The real part 192 and the imaginary part 193 of the deconvolved upper edge signal are also represented, the upper edge signal being considered as reference representing a clean edge of a plate.

It shows for the real part of the deconvolved lower edge signal a positive peak 194 corresponding to the passage of clean plate, and a negative peak 195 corresponding to the presence of a fouling break. A negative peak 196 is reproduced for the imaginary part of the deconvolved lower edge signal. The expected absence of peak corresponding to the passage from the edge of clean plate should be noted for the imaginary part.

The examples could again be multiplied. It may be deduced therefrom that the method according to the invention makes it possible to interpret physically the profiles of the deconvolved complex signal. Simple indicators may be put forward to deduce the condition of the foliated passages of a tube support plate. Actually, the deconvolved complex signal represents directly the condition of the tube support plate through the different types of variation of impedance that it highlights.

For a clean tube support plate, the imaginary part of the deconvolved complex signal has zero power.

In the presence of a clogged lower edge of plate:
the imaginary part of the deconvolved lower edge signal has high power;
the imaginary part of the deconvolved lower edge signal does not have a constant sign;
the imaginary part of the deconvolved lower edge signal contains as much power in its positive as in its negative values.

Other configurations may also be detected. For example, in the case of a fouled tube, a fouling break in the vicinity of the tube support plate may be detected by the fact that:
the imaginary part of the deconvolved complex signal has considerable power;
the imaginary part of the deconvolved complex signal is of constant sign.

Thus, the method according to the invention makes it possible to considerably improve the evaluation of the condition of clogging of foliated passages, by making it possible in particular to distinguish different configurations, for example a fouling break which could pass for clogging with less precise methods.

More precisely, indicators may be defined to facilitate the analysis of the lower edge signal. The analysis of the deconvolved lower edge signal may thus comprise the definition of indicators corresponding to pairs of extremes of physical quantities of the imaginary part of the lower edge signal. For example, the following indicators may be used for the estimation of clogging or fouling:

If y+ (respectively y−) designates the positive (resp. negative) values taken by the imaginary part of the signal obtained in the vicinity of the lower edge of the plate after deconvolution, and if the following different quantities are defined:

$E_{y+}/E_{y-}$: energy of $y_+$ and $y_-$
$P_{y+}/P_{y-}$: power of $y_+$ and $y_-$
$M_{y+}/M_{y-}$: maximum value of $y_+$ and $|y_-|$
$\Gamma_{y+}/\Gamma_{y-}$: standard deviation of the values taken by $y_+$ and by y.

For each pair of physical quantities, $X_{y+}/X_{y-}$, with X corresponding to E, P, M or $\Gamma$, a minimal indicator and a maximal indicator are defined:
$X_{min}=\min\{X_{y+}, X_{y-}\}$
$X_{max}=\max\{X_{y+}, X_{y-}\}$ According to the preceding interpretations, there is a simple correspondence between the indicators $X_{min}$, $X_{max}$ and the condition of the plate:
Clean tube support plate: $X_{min}$ and $X_{max}$ are low;
Fouling break in the vicinity of the lower edge: $X_{min}$ is low, $X_{max}$ is high;
Lower edge clogged: $X_{min}$ and $X_{max}$ are high and approximately equal.

Other indicators can also be used, by regarding the projection of the deconvolved lower edge signal over a family of functions (Gaussian functions for example).

The invention also relates to a computer programme product comprising programme code instructions saved on a support that can be used in a computer for the execution of the processing steps of the method for evaluating clogging, when said programme is run on a computer.

Actually, the measurement signal is transmitted from the eddy current probe to a memory to be stored therein with a view to its processing. Said processing of the measurement signal on which the present invention is based is implemented by a processing unit equipped with a calculator, typically a computer provided with display and communication means, through which it acquires the measurement signal and transmits the results of the implementation of the method for evaluating clogging, said computer being configured to implement the method according to the invention.

The invention claimed is:

1. Method for adapting an operation of a tube heat exchanger by evaluating clogging of passages of a tube support plate of the tube heat exchanger, said passages being made along tubes of the heat exchanger for a fluid to pass through the tube support plate, the method comprising:

passing an eddy current probe along a tube of the heat exchanger, said eddy current probe passing a downstream edge of the tube support plate and an upstream edge of the tube support plate, and acquiring a measurement signal with the eddy current probe while passing the downstream edge and the upstream edge of the tube support plate, said measurement signal comprising a lower edge signal corresponding to the probe passing a downstream edge of the tube support plate and an upper edge signal corresponding to the probe passing an upstream edge of the tube support plate, transmitting the measurement signal from the eddy current probe to a memory and storing the measurement signal thereon, the method further comprising:

processing of the measurement signal performed by a computer accessing the measurement signal stored in the memory, determining from the measurement signal the lower edge signal corresponding to the probe passing the downstream edge of the tube support plate, determining from the measurement signal the upper edge signal corresponding to the probe passing the upstream edge of the tube support plate, obtaining an estimate of an impulse response of the probe from the upper edge signal, deconvolving the lower edge signal using said estimate of the impulse response derived from the upper edge signal, thereby obtaining a deconvolved lower edge signal, calculating indicators evaluating the clogging at the downstream edge of the tube support plate through analysis of the deconvolved lower edge signal, and outputting said indicators and evaluating the clogging of the passages of the tube support plate from said indicators, wherein the method further comprises adapting an operation of the tube heat exchanger depending on the clogging of the passages of the tube support plate thus evaluated.

2. The method of claim 1, in which the eddy current probe acquires at least in part the measurement signal in differential mode.

3. The method of claim 1, in which the measurement signal is a multifrequency signal composed of at least two signals at different frequencies, and the lower edge signal and the upper edge signal result from linear combinations of at least two signals of the measurement signal at different frequencies.

4. The method of claim 3, in which the linear combination involves at least one complex coefficient optimised to minimise a signal power along the tube outside of plate zones.

5. The method of claim 1, in which the deconvolution of the lower edge signal using the estimate of the impulse response of the eddy current probe is carried out using a filter constructed from said estimate of the impulse response.

6. The method of claim 5, in which the frequency response of the filter is an approximation of the inverse of the Fourier transform of the estimate of the impulse response of the eddy current probe.

7. The method of claim 5, in which the filter is a Wiener filter and the deconvolution is a Wiener deconvolution.

8. The method of claim 7, in which the frequency response of the Wiener filter is of the form:

$$G[f] = \frac{H^*[f]}{\|H[f]\|^2 + \frac{B[f]}{S[f]}}$$

with the exponent * designating a complex conjugation, H[f] a Fourier transform of the estimate of the impulse response of the eddy current probe, S[f] a power spectral density of a signal to be estimated and B[f] a power spectral density of noise.

9. The method of claim 1, in which a filtering by a low pass filter is applied to the deconvolved lower edge signal, the cut-off frequency of said low pass filter being determined from a standard deviation of a Gaussian function constituting an approximation of a real part of an impulse of the signal corresponding to the eddy current probe passing a clean edge of tube support plate.

10. The method of claim 1, in which analysis of the deconvolved lower edge signal comprises the analysis of a real part and an imaginary part of said deconvolved lower edge signal.

11. The method of claim 1, in which calculated indicators correspond to pairs of extrema of physical quantities of an imaginary part of the deconvolved lower edge signal.

* * * * *